United States Patent [19]

Babayan et al.

[11] Patent Number: 5,175,339
[45] Date of Patent: Dec. 29, 1992

[54] PROCESS FOR PREPARING SOLID PARTICULATE DIALKYLESTERS FROM THEIR CORRESPONDING DIANHYDRIDES

[75] Inventors: Eduard P. Babayan, Huntington Beach; Douglas G. Soden, Santa Ana; Anthony Bosch, El Toro, all of Calif.

[73] Assignee: The Standard Oil Company, Cleveland, Ohio

[21] Appl. No.: 522,622

[22] Filed: May 14, 1990

[51] Int. Cl.$^5$ .............................................. C07C 69/76
[52] U.S. Cl. ........................................ 560/52; 560/64; 560/59; 560/76; 560/96
[58] Field of Search ................ 560/52, 64, 59, 76, 560/96

[56] References Cited

U.S. PATENT DOCUMENTS

| | | | |
|---|---|---|---|
| 3,420,795 | 1/1969 | Angelo | 260/47 |
| 3,422,076 | 1/1969 | Petropoulos | 260/78.4 |
| 3,506,583 | 4/1970 | Boram et al. | 252/188.3 |
| 3,745,149 | 7/1973 | Serafini et al. | 260/65 |
| 4,206,106 | 6/1980 | Heilman et al. | 260/30.2 |
| 4,206,107 | 6/1980 | Chow | 260/30.2 |
| 4,244,853 | 1/1981 | Serafini | 260/33.4 |
| 4,255,488 | 3/1981 | Gagliani | 428/398 |
| 4,296,208 | 10/1981 | Gagliani et al. | 521/77 |
| 4,506,038 | 3/1985 | Gagliani et al. | 521/103 |
| 4,539,336 | 9/1985 | Long et al. | 521/77 |
| 4,546,115 | 10/1985 | Gagliani et al. | 521/77 |
| 4,621,015 | 11/1986 | Long et al. | 428/317.7 |

FOREIGN PATENT DOCUMENTS 143127 5/1985 European Pat. Off. .
851205 10/1960 United Kingdom .

OTHER PUBLICATIONS

Lauver, R. et al., 34th Annual Technical Conference (1979) Reinforced Plastics/Composite Institute The Society of Plastic Industry, Inc.
Johnston, J. C. et al., J. of Polymer Science Part A Polymer Chem., vol. 25, 2175-2183 (1987).
Handbook of Composites, George Lubin, edit. (1982).
Serafini, T. T. et al., J. of Applied Polymer Science, vol. 16, pp. 905-915 (1972).
Alvino, W. et al., J. of Applied Polymer Science, vol. 22, 1983-1990 (1978).

Primary Examiner—Paul J. Killos
Attorney, Agent, or Firm—Michael F. Esposito; Larry W. Evans

[57] ABSTRACT

A process for producing a dialkyl ester (i.e. BTDE) from its corresponding dianhydride (i.e., BTDA) comprising mixing the dianhydride, an organic solvent, solid catalyst and an alcohol capable of reacting with the dianhydride stirring the solution until the dianhydride and alcohol have reacted to form the dialkyl ester, separating the dialkyl ester from the catalyst and drying the ester to form a solid paticulate product. The product has a purity of over 85%.

14 Claims, No Drawings

PROCESS FOR PREPARING SOLID PARTICULATE DIALKYLESTERS FROM THEIR CORRESPONDING DIANHYDRIDES

BACKGROUND OF THE INVENTION

The present invention is directed to a process for producing solid particulate dialkylesters from their corresponding dianhydrides. In particular, the present invention is directed to the production of the dimethylester of benzophenonetetracarboxylic acid (BTDE) from benzophenonetetracarboxylic dianhydride (BTDA). BTDE has specific utility in the formation of polyimide resins used to produce reinforced high temperature fabrics.

The polyimide resins to which the present invention relates are noted for their high thermal and oxidative stability, high strength at elevated temperatures, and many other outstanding physical and chemical properties useful in high temperature applications such as jet engine compression components, for example blades, vanes, air seals, air splitters and engine casing parts. The method for preparing high molecular weight addition type polyimides is described in U.S. Pat. No. 3,745,149 herein incorporated by reference.

In general the method for preparing the polyimides includes forming a mixture of a polyfunctional amine, a polyfunctional ester and an end-capping agent. In particular, esters of tetracarboxylic acid produced from corresponding dianhydrides are shown as useful in the production of the polyimide resin. While the end-capping agent and the polyfunctional amine are available in 100% solid component, the polyfunctional ester, typically BTDE, has always been prepared and sued from an alcohol solution, typically methanol. This procedure for preparation of BTDE generates detrimental quantities of the tri-or tetra- ester over time due to the presence of excess alcohol. Therefore, because of the storage instability, the BTDE solution had to be prepared on site and/or had to be used within a certain period of time to provide the resulting polyimide resin with its proper properties.

The present invention is directed to providing a method of manufacturing BTDE in solid form. The advantages of the invention are that the BTDE prepared by the process of the present invention contains substantially less undesirable bi-coproducts because excess alcohol is not present. Furthermore, the BTDE because it is in solid form is stable and can be stored for indefinite period. Finally, because the solid BTDE does not require the presence of methanol other polyfunctional amines which have not been able to be used because of their insolubility in methanol can now be used to develop different polyimide resins which will have new properties.

SUMMARY OF THE INVENTION

It is the primary object of the present invention to provide a method for the production of solid dialkylesters from corresponding dianhydrides.

It is a further object of the present invention to provide solid BTDE from BTDA.

It is still another object of the present invention to provide a substantially pure solid product comprising BTDE.

Additional objects, advantages and novel features of the invention will be set forth in part in the description which follows, and in part will be become apparent to those skilled in the art upon examination of the following or may be learned by practice of the invention. The objects and advantages of the invention may be realized and obtained by means of the instrumentalities and combinations, particularly pointed out in the appending claims.

To achieve the foregoing and other objects and in accordance with the purpose of the invention as embodied and broadly described herein the process of preparing the dialkylester from its corresponding dianhydride comprises mixing together the dianhydride, an organic solvent, an alcohol capable of reacting with the dianhydride to produce the dialkyl ester and a catalyst, stirring the mixture until the alcohol has reacted with the dianhydride to produce the dialkyl ester (usually indicated by the solution becoming clear), separating the dialkyl ester from the catalyst, and drying the dialkyl ester to produce a solid particulate dialkyl product. Preferably, the organic catalyst is in solid form (i.e. incorporated into a polymer backbone) and not soluble in the organic solvent. Especially preferred catalyst are polymeric organic solid catalyst which are not soluble in the organic solvent.

In a further preferred embodiment of the present invention the process comprises producing a substantially pure dimethylester of benzophenonetetracarboxylic acid (BTDE) in solid particulate form comprising mixing benzophenonetetracarboxylic dianhydride (BTDA), an organic solvent, methanol and a polymeric organic solid catalyst to form a solution, stirring the solution until the methanol has reacted with the BTDA to produce BTDE (usually indicated by the solution turning clear), separating the solid catalyst from the BTDE, drying the BTDE to obtain substantially pure BTDE in solid particulate form.

DETAILED DESCRIPTION OF THE INVENTION

The present invention is directed to the process of producing a solid dialkyl, (i.e., $C_1$ to $C_4$) ester from its corresponding dianhydride comprising combining the dianhydride of the desired dialkyl ester, a low boiling solvent, an alcohol selected from the group consisting of methanol, ethanol propanol and butanol and a solid catalyst insoluble in the low boiling solvent, stirring the solution until the dianhydride has reacted with the alcohol to produce the corresponding dialkyl ester, separating the dialkyl ester from the solid catalyst and drying the dialkyl ester to produce substantially pure dried particulate product.

In a preferred embodiment of the present invention the alcohol is selected from the group consisting of methanol and ethanol, most preferably the alcohol is methanol.

In a preferred embodiment of the process of the present invention the alcohol is utilized in its anhydrous form.

In another preferred embodiment of the present invention the organic solvent is an organic solvent having a boiling point below 110° C. For example, acetone, methylene chloride and dioxane are suitable in the practice of the present invention. The particular organic solvent is not critical provided that the solvent does not in any way interfere with the reaction of the alcohol with the dianhydride to produce the dialkyl ester. Low boiling organic solvents are preferred because they can be removed from the dialkyl ester by low temperature drying procedures (e.g. spray drying).

In still another preferred embodiment of the present invention the separation of the dialkyl ester from the solid catalyst is performed by filtration.

In a still further preferred embodiment of the present invention the solid catalyst materials is a tertiary amine catalyst such as DMAP (4-dimethylamino pyridine) which has been insolubilized by incorporation into a polymer backbone. Commercial catalyst products such as Reillex 425 and Reillex Poly DMAP 404 available from Reilly Industries, Inc. are suitable catalyst material.

In another preferred embodiment of the present invention the dried solid particulate dialkyl ester to reflux temperature. The dried particulate dialkyl ester can be obtained then by spray drying at the appropriate temperature depending on the solvent use.

In particular, the process of the present invention is directed to the production of the solid substantially pure particulate dimethylester of BTDA comprising combining BTDA, methanol, a low boiling organic solvent and a solid-polymer bead catalyst which is insoluble in the organic solvent to form a solution, stirring the solution until the dianhydride has reacted with the methanol to form BTDE, filtering the mixture to remove the solid polymeric catalyst beads to obtain a filtrate substantially free of catalyst, drying the filtrate to obtain the substantially pure particulate BTDE.

Other dimethyl esters of corresponding dianhydrides may be prepared by the practice of the process of the present invention. For example, the dimethyl esters of biphenyltetracarboxylic dianhydride (BTDA), pyromellitic dianhydride (PMDA), and oxydiphthalic dianhydride (ODPA) may all be prepared by the process of the present invention.

The process of the present invention produces solid particulate dialkyl ester product having a purity of at least 85%. Typical analysis indicates that in the BTDE produced by the process of the present invention is 90 to 95% pure.

An important aspect to the practice of the process of the present invention is that it enables the manufacture of the dialkyl ester without using a substantial excess of alcohol. The process of the present invention utilizes sufficient alcohol to enable the reaction of the dianhydride to proceed to the dialkyl ester but insufficient alcohol to allow for the reaction to continue to produce undesired tri or tetra ester. For example, the process of the present invention is usually performed using no more than 0.5 mole excess of alcohol (i.e. methanol). This assures that the reaction of the dianhydride with the alcohol proceeds only to the corresponding dialkyl ester and does not continue to produce the undesired tri- or tetra- ester to any significant degree.

For illustrative purposes only the following examples are provided to further describe the process of the present invention.

EXAMPLE 1

In a 30 gallon polyethylene container equipped with a stirrer was placed anhydrous acetone (23.2 kg), BTDA (22.7 kg), anhydrous methanol (5.4 kg), and 4-(4-methyl-1-piperidinyl) pyridine (0.83 kg). A mildly exothermic reaction ensued increasing the temperature to near reflux for a few minutes. The reaction mixture was stirred at ambient temperature for two hours, after which time the solution was clear and the reaction was complete. High Performance Liquid Chromography (HPLC) analysis indicated the presence of benzophenonetetracarboxylic acid (0.1%, monoester 0.4%, diester 99.3% and triester 0.2%. To remove the catalyst, ion exchange resin (3 kg, Dowex 50dialkyl-X8, H+) was added and the mixture stirred for five hours, followed by filtration. The bulk of the filtrate was slowly poured into approximately 40 liters of hexane with vigorous stirring. The syrupy produce which settled out was separated by draining and placed on trays in a large vacuum oven and dried at 45°-50° C. The product (25.1 kg) was obtained as a hard, glassy, amorphous solid, readily broken into small pieces.

In view of the cumbersome precipitation method, hexane recovery/disposal and the lengthy drying time required to obtain a solvent free product, a few liters of the above acetone filtrate were diluted further to 10-20% solids content and aspirated through a commercially available lab sized spray dryer (Buchi/Brinkmann mini spray dryer, Model #190). The BTDE was isolated as a dry fine, pale-yellow solid with particle size of mostly under 25 microns.

EXAMPLE 2

In order to avoid the use of a soluble catalyst followed by subsequent removal by precipitation, extraction, or ion exchange (and ion exchange resin regeneration), a tertiary amine catalyst 4-dimethylamino pyridine insolubilized by incorporation into a polymer backbone was used. Commercial products such as Reillex 425 and Reillex Poly DMAP 404, available from reilly Industries, Inc. are suitable materials. A dry 125 ml flask was charged with BTDA (32.2 g, 0.1 mole), anhydrous acetone (56.6 g), anhydrous methanol (7.7 g, 0.24 mole) and dried Reillex Poly DMAP 404 (10 g). Prior to using the catalyst, which contained 45% toluene, was washed free of this solvent by soaking it three times in dry acetone followed by filtration. The mixture was stirred at room temperature for 72 hours, after which time all the starting materials had gone into solution. After an additional 48 hours at room temperature, the catalyst was recovered by filtration. HPLC analysis of the filtrate indicated the following composition: BTDE 97.7%, monoester, 2.9%, other 0.4%.

EXAMPLE 3

A dry, 125 ml flask was charged with BTDA (32.2 g, 0.1 mole), anhydrous acetone (56.6 g), anhydrous methanol (7.7 g, 0.24 mole) and dried Reillex Poly DMAP 404 (5.5 g, 0.0077 equivalent of DMAP). The catalyst had been freed of solvent by overnight drying in a vacuum oven at 105°-110° C. The reaction mixture was stirred at room temperature for 48 hours after which time the solution was clear. The catalyst was recovered by filtration and was washed with dry acetone. After air drying at room temperature for 30 minutes, the weight was 12 g. HPLC analysis of the filtrate showed the following composition: BTDE 88.7%, monoester 11.1%, other 0.2%.

EXAMPLE 4

The procedure described in Example 3 was repeated, except that the reaction mixture was refluxed. After approximately two hours, the solution was clear. HPLC analysis: BTDE 92.0%, monoester 7.9%, other 0.2%. The weight of recovered catalyst, after overnight drying in a vacuum oven at 105°-110° C., was 9.7 g, indicating the presence of absorbed product, probably in the form of a weak acid-base salt.

The effectiveness of the catalyst was shown by repeating the reaction in the absence of the Reillex Poly DMAP 404. Even after 24 hours at reflux temperature, a large proportion of the BTDA was still undissolved and unreacted.

EXAMPLE 5

The procedure described in Example 3 was repeated, except that only half the amount of dried catalyst was used. After stirring 72 hours at room temperature, the reactants had dissolved and the solution was clear. HPLC analysis: BTDE 89.6%, monoester 10.4%.

EXAMPLE 6

The procedure described in Example 3 was repeated, except that methylene chloride (80 g) was used as the solvent. The reaction mixture was refluxed for 5 hours, after which time the solution was clear. HPLC analysis: BTDE 95.6%, monoester 3.3%, triester 0.5%, other 0.6%.

EXAMPLE 7

To a 100 ml flask was added BTDA (16.1 g, 0.05 mole), anhydrous methanol (29 g) and dried Reillex Poly DMAP 404 (2.8 g, 0.0038 equivalent of DMAP). After stirring for 30 hours at room temperature, the reaction solution became clear. HPLC analysis: BTDE 99.3%, monoester 0.3%, triester 0.4%.

EXAMPLE 8

A 100 ml flask was charged with BTDA (16.1 g, 0.05 mole), anhydrous acetone (28.3 g) anhydrous methanol (2.99 g, 0.09 mole) and dried Reillex Poly DMAP 404 (2.8 g). The mixture was stirred at room temperature and cleared after 72 hours. After an additional 24 hours of stirring, BPLC analysis was as follows: BTDE 86.7%, monoester 12.8%, other 0.5%.

EXAMPLE 9

To a 125 ml flask was added BTDA (32.2 g, 0.1 mole), anhydrous acetone (56.6 g), anhydrous methanol (7.7 g, 0.24 mole, and the Reillex Poly DMAP 404 catalyst (12 g) recovered from the experiment described in Example 3. The mixture was stirred at room temperature and became clear after 40 hours. HPLC analysis: BTDE 93.9%, monoester 6.1%.

The catalyst from this reaction was recovered again by filtration and washed with dry acetone, and was used directly again in a similar experiment. Results were nearly identical, indicating that the catalyst can be recycled without any special treatment.

The foregoing description of the preferred embodiments of the invention has been presented for purposes of illustration and description. It is not intended to be exhaustive or limit the invention to the precise form disclosed and obviously many modifications and variations are possible in light of the disclosure. The embodiments were chosen and described in order to best explain the principles of the invention and its practical application to thereby enable others skilled in the art to est utilize the invention in various embodiments and with various modifications as are suited to the particular use contemplated. It is intended that the scope of the invention be defined by the claims appended hereto.

What we claim is:
1. A method for producing a solid particulate $C_1$ to $C_4$ dialkyl esters from its corresponding dianhydride comprising:
   a. mixing the dianhydride, an organic solvent, an alcohol capable of reacting with said dianhydride to produce said dialkyl ester and a catalyst to form a solution wherein said alcohol is present in said solution in an amount sufficient to enable production of said dialkyl ester but insufficient to allow production of substantial amounts of the corresponding trialkyl or tetraalkyl ester;
   b. stirring said solution until said dianhydride has reacted with said alcohol to produce said dialkyl ester;
   c. separating said dialkyl ester from said catalyst; and
   d. drying said dialkyl ester to produce a substantially pure particulate product.

2. The process of claim 1 wherein said catalyst is insoluble in said solvent.

3. The process of claim 2 wherein said dianhydride is selected from the group consisting of benzophenonetetracarboxylic dianhydride (BTDA), biphenyltetracarboxylic dianhydride pyromellitic dianhydride and oxydiphthalic dianhydride.

4. The process of claim 2 wherein said alcohol selected from the group consisting of methanol, ethanol, isopropanol and butanol.

5. The process of claim 4 where said alcohol is methanol.

6. The process of claim 5 wherein said dianhydride is BTDA.

7. The process of claim 1 wherein said alcohol is added to said solution in an amount no greater than 0.5 moles in excess of amount needed to react with said dianhydride to form said diester.

8. The process of claim 1 wherein said catalyst is a tertiary amine.

9. A process for producing the solid particulate dimethylester of benzophenonetetracarboxylic acid (BTDE) comprising mixing benzophenonetetracarboxylic dianhydride (BTDA), an organic solvent, methanol and a polymeric organic solid catalyst to form a solution wherein the methanol is present in said solution in an amount sufficient to enable production of the dimethyl ester but insufficient to allow production of substantial amounts of the corresponding trialkyl of tetraalkyl ester, stirring said solution until said methanol has reacted with the BTDA to form BTDE, separating the BTDE from said catalyst, and drying the BTDE to obtain a solid particulate product.

10. The process of claim 9 wherein the organic solvent is selected from the group consisting of acetone, methylene chloride and dioxane.

11. The process of claim 9 wherein said BTDE is separated from said catalyst by filtration.

12. The process of claim 11 wherein said solid particulate BTDE is obtained by spray drying.

13. The process of claim 9 wherein said solid catalyst is a tertiary amine which has been insolubilized by incorporation into a polymer backbone.

14. The process of claim 11 wherein the alcohol is added to said solution in an amount no greater than 0.5 moles in excess of amount needed to react with said dianhydride to form said diester.

* * * * *